United States Patent [19]

Chevalier

[11] Patent Number: 4,490,609

[45] Date of Patent: Dec. 25, 1984

[54] METHOD AND APPARATUS FOR ANALYZING WELL FLUIDS BY PHOTON IRRADIATION

[75] Inventor: Philippe Chevalier, Verrieres le Buisson, France

[73] Assignee: Schlumberger Technology Corporation, Houston, Tex.

[21] Appl. No.: 391,320

[22] Filed: Jun. 23, 1982

[51] Int. Cl.³ .............................................. G01V 5/12
[52] U.S. Cl. ................................... 250/269; 250/266; 378/89
[58] Field of Search ............... 250/264, 265, 266, 269, 250/301; 378/88, 89, 124

[56] References Cited

U.S. PATENT DOCUMENTS

| | | | |
|---|---|---|---|
| 2,881,324 | 4/1959 | Scherbatskoy | 250/264 |
| 3,015,030 | 12/1961 | Jones | 250/269 |
| 3,038,075 | 6/1962 | Youmans | 250/266 |
| 3,058,000 | 10/1962 | Scherbatskoy | 250/269 |
| 3,123,709 | 3/1964 | Caldwell et al. | 250/269 |

Primary Examiner—Alfred E. Smith
Assistant Examiner—Carolyn E. Field

[57] ABSTRACT

The invention relates to a method of measuring the absorption of a photon flux in the fluid flowing in an oil well, for the purpose of determining the composition of the fluid. The invention also relates to a logging sonde for implementing such method.

The photon flux produced by a source such as an X-ray generator irradiates the entire volume of fluid surrounding the sonde, and the energy of the photons is lower than a predetermined value, preferably 100 kev, so that the walls of the well are capable of substantially absorbing the photons impinging thereon. The photon flux includes an energy level at which photoelectric absorption is significant and another energy level at which Thomson scattering is predominant. Measurements of the photoelectric absorption coefficient and density are used to determine water, oil, and salinity.

22 Claims, 11 Drawing Figures

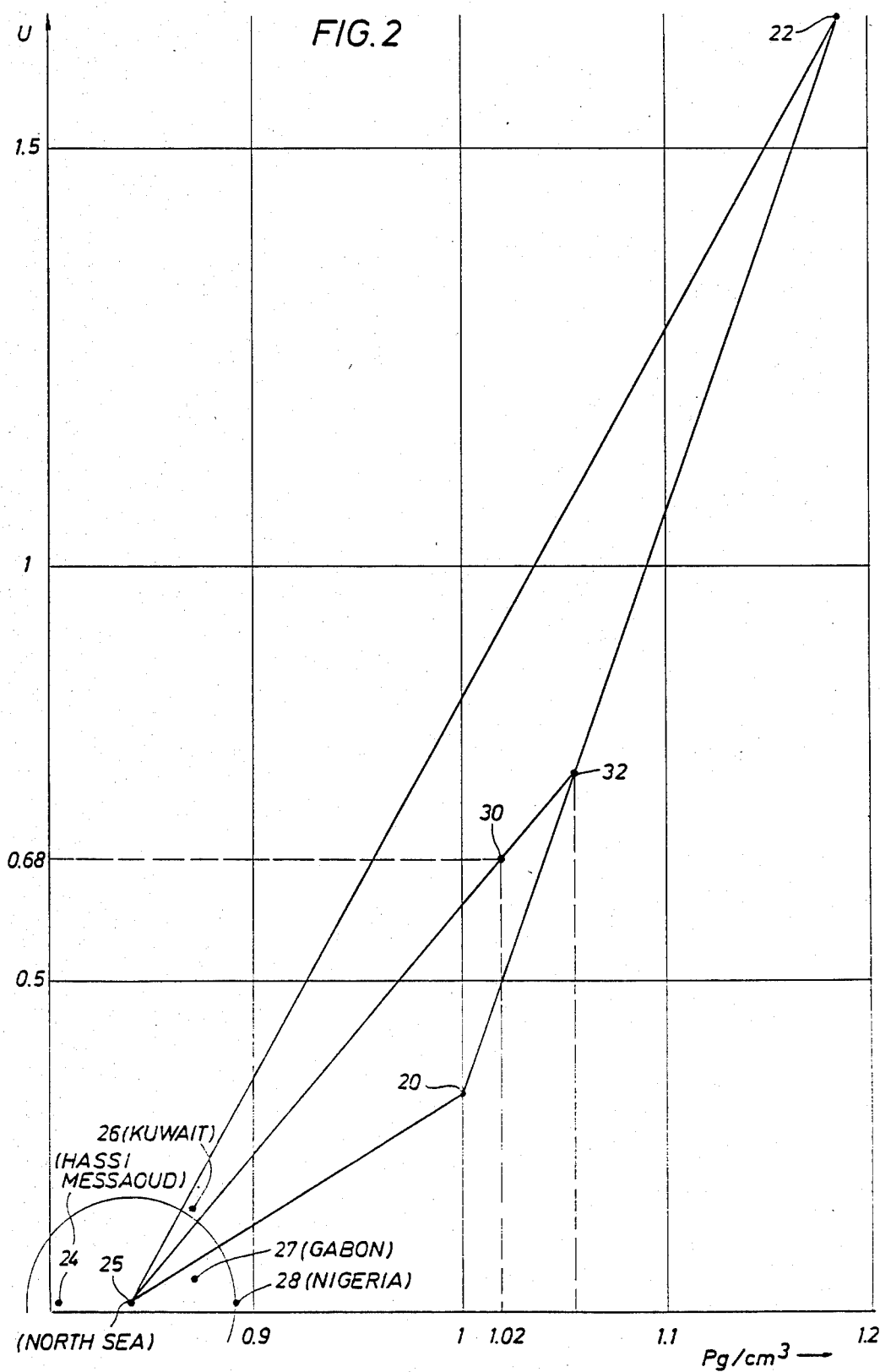

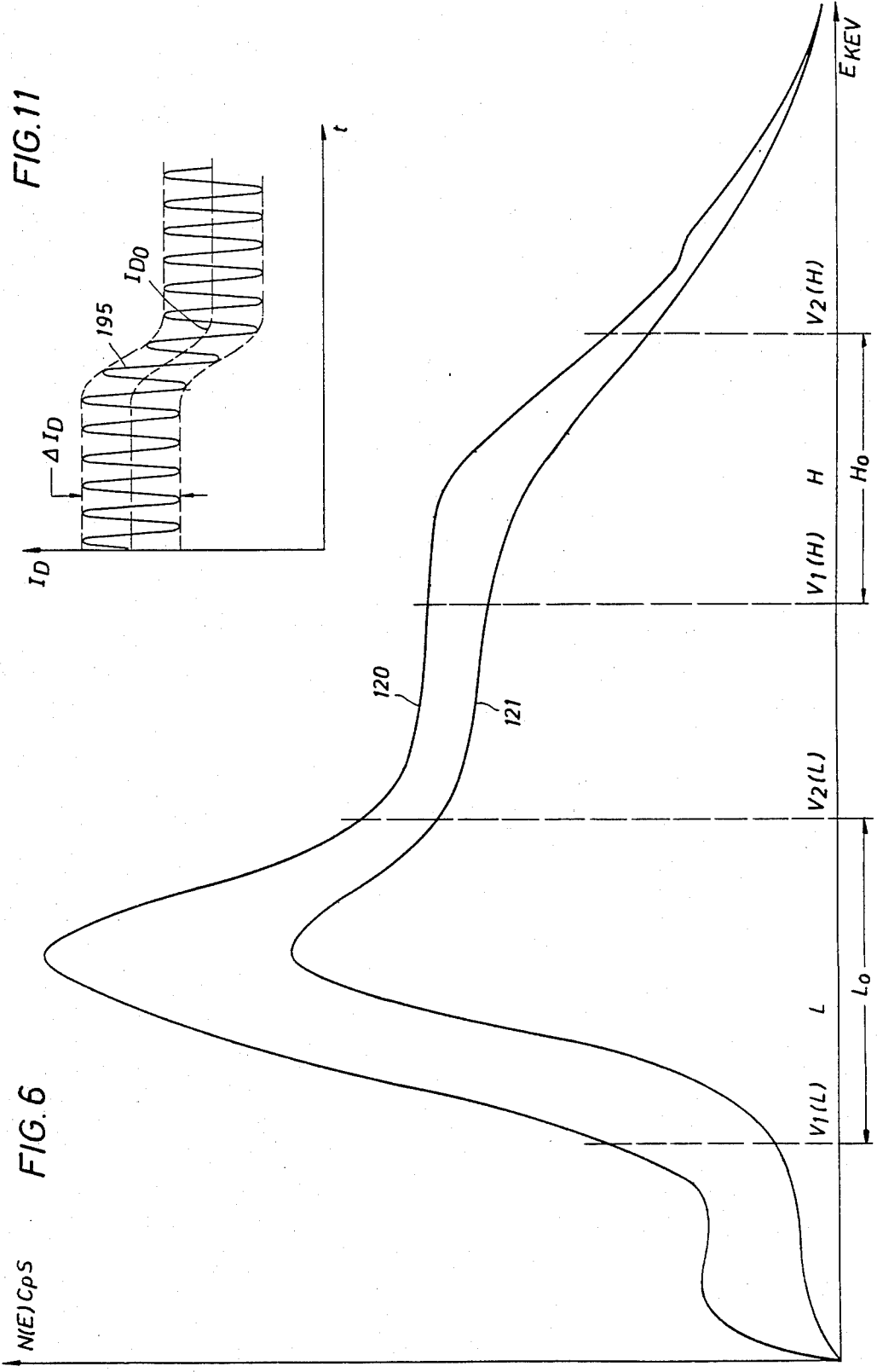

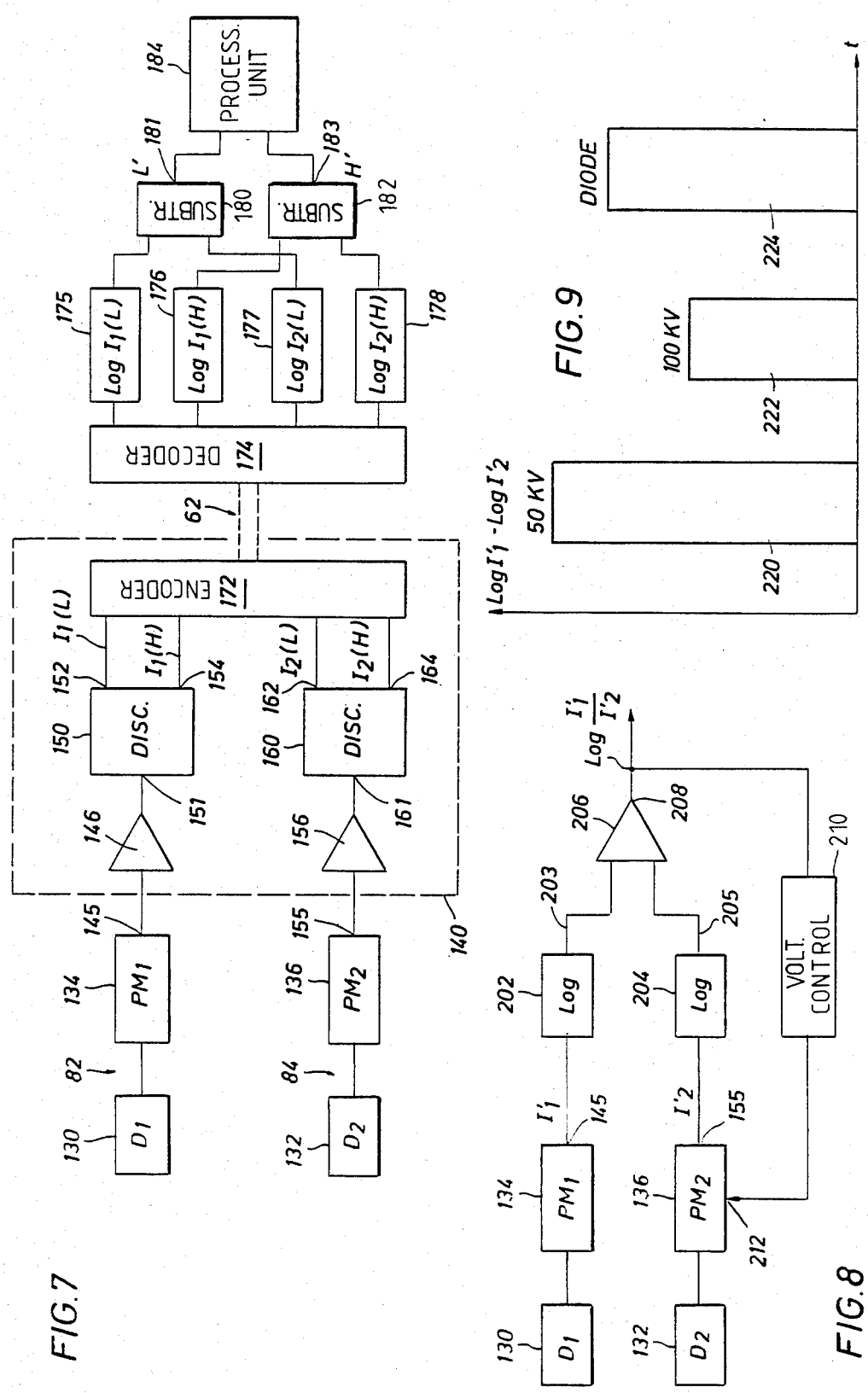

METHOD AND APPARATUS FOR ANALYZING WELL FLUIDS BY PHOTON IRRADIATION

BACKGROUND OF THE INVENTION

The invention relates to the analysis of the fluid in an oil well and more particularly to the measurement of the photon absorption properties of the well fluids such measurement providing indications as to the composition of the fluid.

There is disclosed in U.S. Pat. No. 2,961,539 to Egan et al a sonde for determining the density of fluid in a well bore, comprising a source of gamma rays and a gamma ray detector spaced from the source, with a gamma ray absorbing shield disposed in the direct path from the source to the detector. The flux produced by the source thus irradiates the fluid outside the sonde.

It is pointed out in this patent that some of the photons striking the detector have been scattered from the formation traversed by the well back to the detector. Under such conditions, an accurate measurement cannot be obtained.

In order to deal with this problem, the above patent teaches disposing about the source and the detector a tubular shield, e.g. of lead, to absorb the photons backscattered from the formations.

However, the presence of such a shield is disadvantageous in that it creates a fluid path separate from the main flow, only this fluid channel being subject to measurement. In this connection, it should be pointed out that the composition of the fluid inside this channel may depart from the compositon in the main flow. This occurs particularly in deviated wells because differences in density of the components of the fluid bring about segregation of these components over the cross-section of the well. This, again, prevents accurate measurements from being obtained.

Another proposal, described in the above patent with reference to FIG. 7 (see also U.S. Pat. Nos. 3,103,812, 3,123,709, 3,688,115; French Pat. Nos. 1,283,068, 1,291,856), consists of measuring the absorption of gamma rays over the direct path from the source to the detector. This requires that a fluid channel be created inside the sonde, with gamma ray absorbing material encompassing the fluid channel. This solution suffers from the same defect as that mentioned above, i.e. the measurement yields information about a very limited sample of the well fluid, which may not be representative of the main fluid flow insofar as the composition is concerned.

In addition, all of the above-mentioned patents merely disclose that the purpose of gamma ray absorption measurements is to determine the density of the well fluid. The fluid in an oil well generally contains a mixture of oil and water, generally saline water. Oil and water have densities which are rather similar, for instance 1 or slightly more for water and 0.8 for oil. This low contrast represents a major limitation in the accuracy of the data obtained. Therefore, when only density data are derived from the measurements of gamma ray absorption and the water/oil ratio is computed from those data, the precision of the result will be mediocre. Moreover, no valuable indication as to salinity can be drawn from density data since the variation of density with salinity is very small.

In Soviet Union Author's Certificate No. 326,904, a method for the determination of salinity is disclosed, in which, in addition to the conventional absorption measurement, the X-fluorescence line of chlorine is detected to determine the amount of chlorine in the water and therefore the salinity. This method is impractical because the fluorescence line of chlorine lies at 2.8 kev, well below the minimum energy capable of being detected by the photon detectors usable in well logging sondes, which is about 20 kev.

SUMMARY OF THE INVENTION

It is therefore an object of the present invention to improve irradiation mixture analysis techniques, notably techniques for determining the composition of hydrocarbon containing media.

In accordance with the invention, the fluid outside the sonde is irradiated with a photon flux having an energy spectrum below a predetermined level such that the walls of the well are capable of substantially absorbing the photons impinging thereon, said level being preferably 100 kev.

Thus the volume subject to absorption measurement is limited to the well since the walls of the well act as a photon absorbing shield and on the other hand it is not restricted to a portion of the well fluid as the entire volume of fluid outside the sonde is irradiated. The measurement will therefore be fully representative of the well fluid.

In a preferred embodiment, a photon flux with a continuous energy spectrum is produced by means of an X-ray generator.

The X-ray generator can be operated to produce an energy spectrum including a lower energy range for which photoelectric absorption by the fluid is significant, and a higher energy range for which Thomson scattering is predominant. Preferably these energy ranges are centered about 30 kev and 60 kev, respectively. By a spectral analysis of the resultant flux, two measurements related to respectively the lower and the higher energy ranges are produced, from which both the photoelectric absorption coefficient and the density of the fluid can be derived. With the knowledge of the densities and the photoelectric absorption coefficients of the components of the fluid, i.e. water and oil, and of the variation of such coefficient with salinity, the amounts of the components as well as the salinity of the water can be determined. The accuracy of the results will be satisfactory owing to the high contrast between oil and saline water insofar as photoelectric absorption is concerned.

BRIEF DESCRIPTION OF THE DRAWINGS

The additional explanations and the description of examples which follow are given with reference to the appended drawings in which:

FIG. 2 is a diagram illustrating the relationships between the density and a parameter characteristic of the photoelectric absorption of compounds of a mixture of hydrocarbons and salt water;

FIG. 6 is a diagram illustrating energy spectra detected from the interaction of the photons emitted by the generator of FIG. 5 with different media;

FIGS. 7 and 8 illustrate two imbodiments of the circuits for detecting and processing the signals delivered by the sonde of FIG. 4;

FIG. 9 is a schematic diagram of an operating sequence of the tool, according to one embodiment;

FIG. 11 is a diagram as a function of time of the signal obtained by means of a sonde according to another embodiment of the invention.

DESCRIPTION OF THE PREFERRED EMBODIMENT

It is known that a medium subjected to a flux $\phi_o$ of incident photons of given energy absorbs these photons in accordance with the distance x traveled, it being possible to express the resulting flux $\phi$ by the relationship:

$$\phi = \phi_o e^{-\mu_t x} \qquad (1)$$

In this relationship, $\mu_t$ is a total attenuation coefficient which varies with the nature of the medium traversed and the energy level of the incident radiation.

In the range of energy radiations lower than 150 kev, the resulting flux is influenced by three distinct physical phenomena, the Thomson effect (coherent scattering), the Compton effect (collision with loss of energy) and the photoelectric effect. The respective parts of these different phenomena vary with the energy level of the incident radiation. It is possible to define, for each of them, on a given energy level, respective coefficients $\mu_p$ for photoelectric absorption, $\mu_s$ for the scattering resulting from the Thomson and Compton effects, and $\mu_a$ for Compton absorption such that:

$$\mu_t = \mu_p + \mu_s + \mu_a \qquad (2)$$

For a given medium, characterized by its mass density and the ratio Z/A of its atomic number and of its atomic mass, the respective influence of the factors which affect the propagation of the radiation through the medium can be defined by the following relationship:

$$\mu_t = N\frac{Z}{A} \rho(\sigma_p + \sigma_s + \sigma_a) \qquad (3)$$

in which N is the Avogadro number and $\sigma_p$, $\sigma_s$ and $\sigma_a$ are the cross-sections of the medium for the energy of the incident photons considered, and the mass density $\rho$ is related to the electron density $\rho_e$ of the medium by the relationship:

$$\rho_e = \left(\frac{Z}{A}\right) \rho$$

Figure 1:
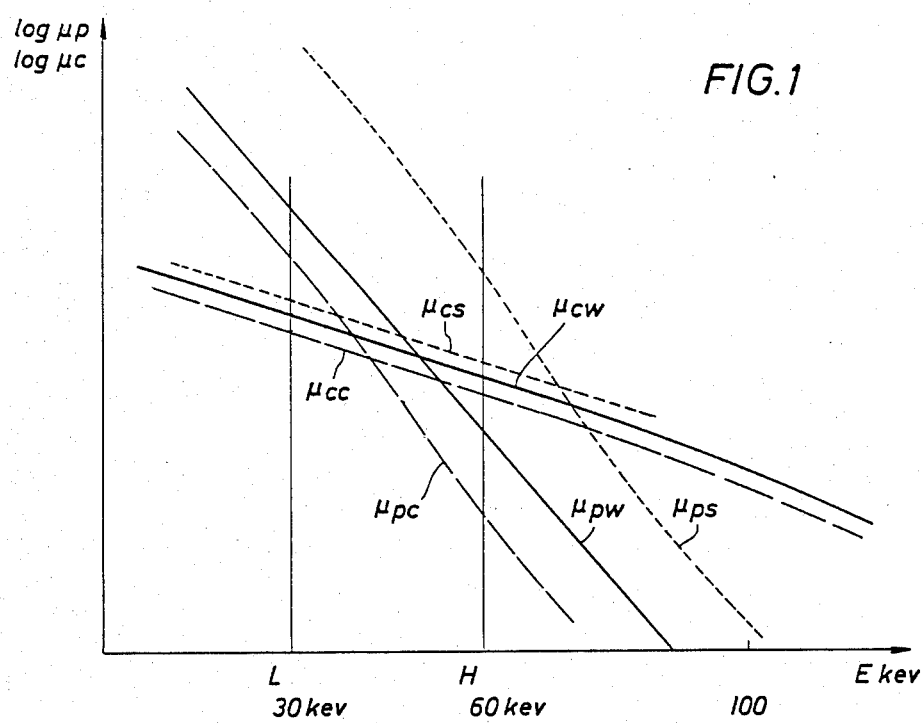
FIG. 1 represents a diagram of photon absorption as a function of photon energy.

FIG. 1 shows a diagram illustrating very schematically the respective contributions on the resulting flux $\phi$ of the photoelectric absorption $\mu_p$, on the one hand, and the combination of the other effects represented by a coefficient $\mu_c = \mu_s + \mu_a$ on the other hand, as a function of the energy E of the incident photons measured in kev.

In the case where the interaction medium is water (solid-line curves), it is noted for example that the part of the photoelectric absorption $\mu_{pw}$ is small in relation to the other effects in the field of relatively high energies. As with most other chemical compounds, the influence of the photoelectric effect does not begin to become substantial until an incident photon energy range lower than 100 kilo-electron-volts. FIG. 1 illustrates the great drop in the photoelectric absorption indicated in logarithmic scale with an increase in the incident photon energy, this absorption being approximately inversely proportional to the cube of the incident energy.

On the other hand, in the same field of energies lower than 100 kilo-electron-volts, the coefficient $\mu_{cw}$ varies much less in accordance with the energy of the incident photons. FIG. 1 also represents the variation in the photoelectric absorptions $\mu_{pc}$ of carbon (broken-line curve) and $\mu_{ps}$ of salt-saturated water (dotted-line curve). Also shown schematically are the variations in $\mu_{cc}$ for carbon (broken-line curve) and $\mu_{cs}$ for salt (dotted-line curve).

In general, for a given energy level, the Thomson and Compton interactions, represented by the coefficient $\mu_c$, vary linearly with the atomic number Z of the elements making up the mixture, i.e. with the electron density of this medium, whereas the photoelectric absorption varies as the 4.6th power of this atomic number. The photoelectric absorption of a medium on a given energy level can be characterized by a coefficient U measured in g.cm$^{-1}$ and defined by the relationship:

$$U = 10 \rho \sigma_p \qquad (4)$$

$\sigma_p$ being the photoelectric cross-section in barns per electron for the energy of 60 kev (the barn is a unit of cross-sectional area equal to $10^{-24}$ cm$^2$), and p1 $\rho$ the density in grams per cm$^3$.

Thus, at 60 kev, the photoelectric absorption coefficient is $\mu_p = $ N Z/A U. For another value of the incident photon energy, the total absorption coefficient can be expressed in the following form:

$$\mu_t = N\frac{Z}{A} (\alpha U + \beta \rho) \qquad (5)$$

in which $\alpha$ and $\beta$ are coefficients which depend essentially on the energy of the incident photons, and U and $\rho$ are parameters characteristic of the considered medium, as is Z/A.

Table I below gives the value of these parameters for a certain number of compounds such as water, salt-saturated water, different liquid hydrocarbon compounds, etc.

TABLE I

|  | $\rho$ | U | Z/A |
| --- | --- | --- | --- |
| Water | 1 | 0.358 | 0.555 |
| NaCl | 2.165 | 10.078 | 0.479 |
| Salt-saturated water | 1.19 | 1.715 | 0.536 |
| Sulphur | 2.070 | 11.240 | 0.499 |
| North Sea Crude | 0.84 | 0.108 | 0.576 |
| Kuwait crude | 0.87 | 0.223 | 0.574 |
| Hassi Messaoud crude | 0.80 | 0.100 | 0.576 |
| Nigerian crude | 0.89 | 0.116 | 0.576 |
| Gabonese crude | 0.87 | 1.138 | 0.576 |

Whereas the contrast between the density of water on the one hand and that of the different crude petroleums mentioned in this table is from 1 to 0.8 or 0.9, it can be see that the coefficient U presents a much greater contrast between water and these different petroleum varieties. This contrast is in fact about 3, except in the case of Kuwait crude petroleum where it is about 2.

A measurement, in particular in combination with the density, of a coefficient characteristic of the photoelectric absorption of a medium to be analyzed, such as that of the coefficient U, can thus furnish a means of detecting with very good accuracy the proportions of the respective compounds of a mixture, for example of petroleum and water.

In accordance with the method described here, one determines a parameter characteristic of the photoelectric absorption of a medium, notably a mixture containing petroleum or other carbonated compounds, by measuring the total absorption of incident photon radiation of at least two different energy levels. At least one of these measurements is carried out at a photon energy level sufficiently low so that the photoelectric absorption plays a significant role in the medium studied. The results of these two measurements are combined in order to obtain at least one value of a parameter characteristic of the photoelectric absorption and, preferably, a measurement characteristic of the density of the medium observed.

The measurement of the parameter U characteristic of the photoelectric absorption and of the density $\rho$ for two different incident photon energies within a relatively low energy range is notably advantageous in petroleum wells in production in order to determine the composition of the fluid flowing in the well. In fact, at these energy levels, and in particular at levels lower than 100 kev, the measurement of absorption in the well is not highly affected by the existence of the medium surrounding the fluids to be analyzed, notably the steel casing, the cement and the geological formation traversed by the well. As the photoelectric absorption of these materials is extremely high, practically all the incident photons which come into contact with this medium are absorbed. No radiation coming from the formation occurs toward the detectors placed in the fluid. As an example, it is shown that for an incident photon energy of 50 kev in iron, the mean free path $(l=1/\mu_p)$ of the photons is l=0.6 mm. At 100 kev, this value is l=3.3 mm, compared with current casing thicknesses of 10 mm.

Thus, the measurements obtained are not affected by variations in casing thickness or other factors depending on the surroundings of the well in which flows the measured fluid.

The low energy level of the photons used for the measurement in accordance with the invention is however not an obstacle to its accuracy. It may in fact be feared that the flux of photons detected for the measurement after interaction with the studied medium in the selected energy bands is difficult to utilize owing to excessive energy degradation due in particular to a high Compton absorption.

In actuality, it has been determined that, at the energy levels considered, the Compton absorption plays a relatively small role and the major part of the energy detected, i.e. not absorbed by photoelectric effect, is scattered by the Thomson effect, i.e. without any resultant photon energy deduction in relation to the incident wave. For an incident photon energy of 50 kev, in pure water for example, the loss of energy contained in the incident beam owing to Compton collisions represents only 8% of the total energy scattered. Consequently, the flux of photons captured after interaction with the investigated medium in the two selected energy intervals, and notably in the lowest, are sufficient to allow a precise measurement.

Obtaining coefficients U and $\rho$ from two measurements on two different incident photon energy levels is possible since the photoelectric absorption, on the one hand, and the Thomson and Compton interactions, on the other, follow very different variation laws (see FIG. 1) according to the incident photon energy, making it possible to obtain a precise determination of these coefficients.

Referring to the relationship (5), it is possible to obtain a measurement of the coefficients U and $\rho$ by measuring the attenuation of the photon flux by interaction with the fluid to be analyzed over a predetermined distance in two distinct selected energy intervals, one of these intervals corresponding to a high energy level and the other to a relatively lower energy level. As an example, it is possible to carry out a first measurement of the flux of photons detected after their interaction with the mixture to be analyzed in the "low" energy interval, centered on 30 kev, and a second measurement in a "high" energy interval centered on 60 kev.

According to one embodiment, the mixture to be studied is irradiated by means of a "chemical" type source comprising a radioactive isotope which emits at least two monochromatic energy lines, at least one of which is located within a relatively low energy range, lower than 100 kev. Several sources exist which meet these conditions, for example barium 133 which furnishes photons at two energy levels, respectively 36 and 81 kev, or americium 241.

It may also be decided to irradiate the mixture to be examined by means of photons whose energy spectrum is known and covers a relatively wide energy range. One measures the attenuation of the photons after interaction with the medium over a given distance, in two distinct energy intervals within the incident energy spectrum.

An X-ray tube can be used advantageously for irradiating the mixture to be analyzed. It is then possible to carry out a measurement in two distinct energy intervals within the emission spectrum of this tube for a given value of its acceleration voltage.

A source of photons variable in energy such as an X-ray generator can also be used to vary with respect to time the spectrum of the photons emitted and to carry out successive measurements of the attentuation of the photons for the different emitted energies in order to obtain the coefficients U and $\rho$. In particular, it is possible to vary, for example, the mean energy of the photons emitted in a continuous manner between a first and a second extreme level by sinusoidal modulation of the acceleration voltage of an X-ray tube. The resulting photon flux is then modulated sinusoidally between two corresponding extreme values whose deviation is essentially a function of the photoelectric absorption of the photons by the analyzed medium. The mean value of this resulting flux depends, for its part, essentially on the density of the medium. From the analysis of this signal can be obtained information on U and $\rho$. If one filters, for example, the measurement signal of the resulting photon flux, the amplitude of its sinusoidal component can furnish a measurement of the photoelectric absorption coefficient U and the level of the dc component can provide a measurement of the density.

The values U and $\rho$ make it possible to determine the composition of a ternary mixture, for example a mixture of water and liquid hydrocarbon in the presence of a third constituent.

Thus, in a three-phase oil, water, gas mixture including respective percentages of $v_1$, $v_2$ and $v_3$ of water, petroleum and gas such that $v_1+v_2+v_3=1$ it is possible to determine the values $v_1$, $v_2$, $v_3$ by using the system of equations:

$$\rho = \rho_w v_1 + \rho_h v_2 + \rho_g v_3 \tag{7}$$
$$U = U_w v_1 + U_h v_2 + U_g v_3$$
$$1 = v_1 + v_2 + v_3$$

In these equations, $\rho$ and U are the values coming from the measurement, $\rho_w$, $\rho_h$, $\rho_g$ are the respective densities of the water and of the liquid and gaseous hydrocarbons present which can be obtained, for example, from Table I, just as $U_w$, $U_h$ and $U_g$ are the values of U in these same substances. If the pressure of the gaseous hydrocarbons is low, the values of $\rho_g$ and $U_g$ can be neglected.

The presence of salt in the water tends to increase the contrast between the photoelectric absorption of the water and that of the petroleum. This observation can be used advantageously if one knows by another method the salinity of the water in the mixture. This can be obtained, for example, by an additional measurement carried out using another type of apparatus or, in the case of a petroleum well in production, by the shut-in of the well until the separation and stabilization of the phases. One then carries out a measurement of the absorption in the fluid downhole to obtain a measurement to make it possible to determine the salinity of the water. It is also possible to perform a measurement in the upper portion of the well where the petroleum has been gathered to determine accurately the parameters characteristic of the density and of the photoelectric absorption when they are not known. In the absence of gas, the method makes it possible to measure directly the respective percentages of petroleum and salt water and the salinity of the water.

In FIG. 2, in which the density is on the abscissa and the coefficient U is on the ordinate, a point 20 is plotted whose components correspond to the values $\rho$ and U for pure water. Also plotted, in the upper right-hand part of the figure, is a point 22 whose coordinates are characteristic of salt-saturated water.

In the lower left-hand part of FIG. 2 are plotted several points 24 to 28 each corresponding to values of $\rho$ and U for a crude petroleum coming from one of the regions of the world indicated in Table I.

The various components of a mixture influence the measurements of the densities and the photoelectric absorption coefficients U linearly in proportion to their content in the mixture. Thus, any measurement carried out in a mixture of North Sea crude petroleum (point 25) and salt water leads to a point representative of the values $\rho$ and U measured such as the point 30 located inside a triangle represented in solid lines and whose apexes are made up of the points 20, 22 and 25.

If we call V the salt water content, (1-V) the oil content, and S the weight of salt in the water in kilograms per liter of solution, the values of V and S can be obtained from the relationships (8) in which the densities are expressed in grams per cubic centimeter (density of pure water $\rho_w=1$):

$$\rho = \rho_h(1 - V) + \left(1 - \frac{S}{0.3}\right) V + \rho_{sw} \frac{S}{0.3} V \tag{8}$$

$$U = U_h(1 - V) + U_w \left(1 - \frac{S}{0.3}\right) V + U_{sw} \frac{S}{0.3} V$$

In these equations, $\rho$ and U are the measurements carried out, $\rho_h$ and $U_h$ are the coordinates of the point for crude petroleum (point 25 in the example of FIG. 2), $U_w$ and $\rho_w$ the ordinates of the point 20, namely $U_w=0.358$ and $\rho_w=1$, and $\rho_{sw}$ and $U_{sw}$ are the coordinates of the point 22.

A description now follows of a logging sonde adapted to be lowered into a well for the purpose of determining the composition of the well fluid.

Figure 3:
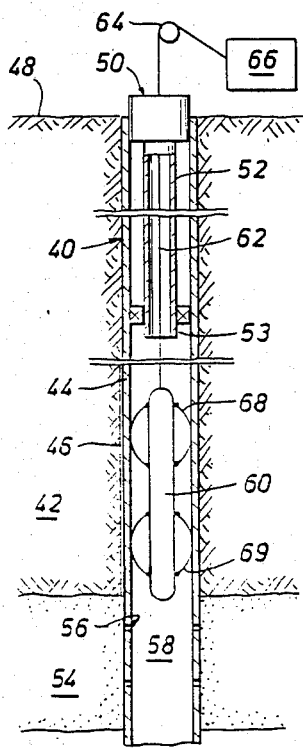
FIG. 3 represents schematically a petroleum well in production, into which a measurement sonde according to the invention has been lowered.

A petroleum well 40 (FIG. 3) traverses, vertically in this example, the geological formations 42. The well is delimited by a steel casing 44. The interval between the casing 44 and the formation 42 is filled with a cement 46 designed to prevent any vertical circulation of fluid to the exterior part of the casing. This casing leads out onto the surface 48. A wellhead, represented schematically at 50, closes off the upper part of the casing and makes it possible to control the flow of fluid inside the production string 52 mounted coaxially within the casing 44 down to a depth in the vicinity of a fluid producing stratum 54. A packer is installed between the end 53 of the production string and the casing to isolate the producing stratum 54. At the level of this stratum, the casing is perforated with openings 56 enabling the flow of the produced fluids into the casing interior 58 for their vertical rise through the production string 52 up to the surface.

In order to determine the fluid flow conditions, their composition and, in general, to monitor the production of the stratum 54, a usual procedure is to lower through the production string 52 logging sondes permitting the appropriate measurements to be carried out. Such a sonde 60 is represented in the space separating the lower end of the production string 52 and the perforations 56. It is suspended at the end of a cable 62 which, on the surface, runs over a pulley 64 at the wellhead and up to an operational unit 66 from which the cable can be wound and unwound. The cable 62, in addition to providing the mechanical suspension for the sonde 60, also carries the electrical connections necessary between the sonde and the operational unit 66.

The diameter of the sonde 60 is sufficiently small to allow its passage within the smaller diameter production string 52, for example 43 mm (1-11/16 inch). It is equipped with upper and lower spring-loaded centering devices 68 and 69 which keep it in a substantially axial position within the casing 44 after it exits the production string 52 over the perforations 56.

Figure 4:
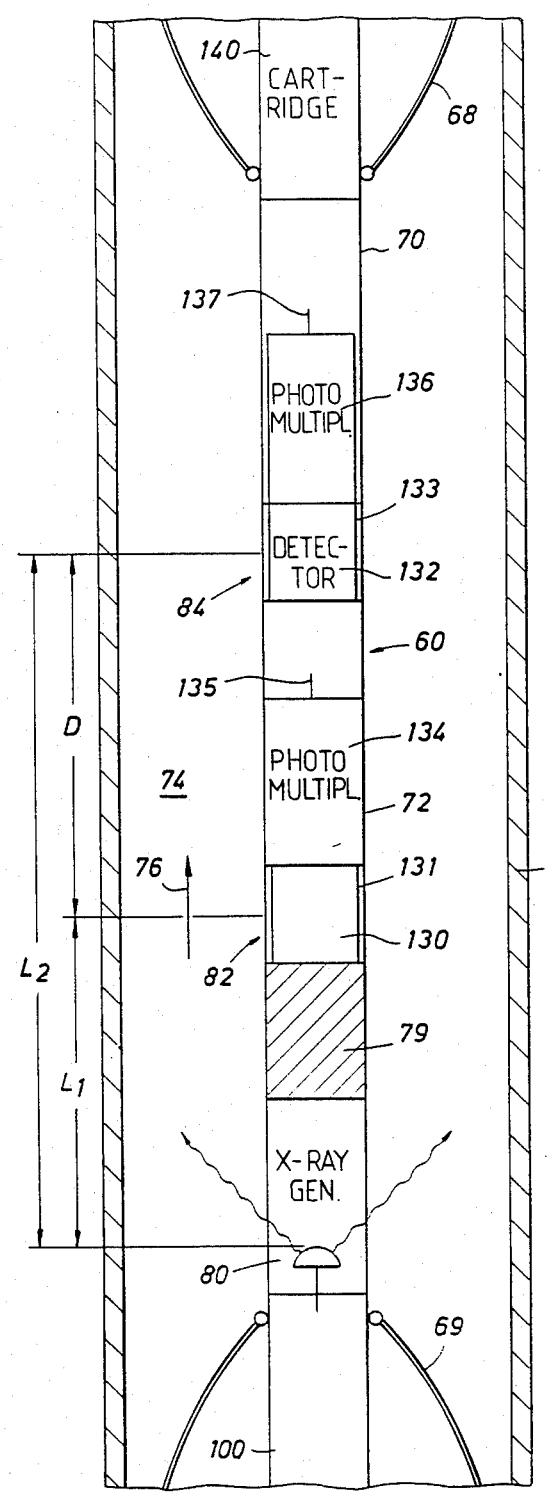
FIG. 4 illustrates schematically the construction of one embodiment of a sonde according to the invention.
Figure 5:
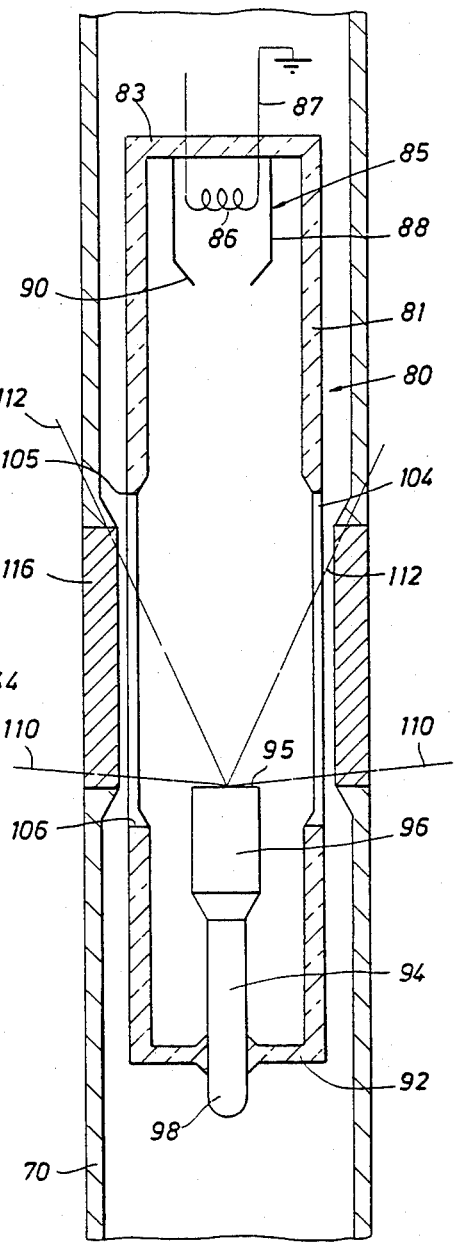
FIG. 5 represents schematically the X-ray generator of the sonde of FIG. 4.

The sonde 60 is designed in the form of an elongated mandrel surrounded by a tubular jacket represented schematically at 70 (FIGS. 4 and 5) capable of resisting the mechanical forces and shocks to which the sonde can be subjected, as well as the temperature and the pressure of the fluids prevailing in the well. Between the upper and lower centering springs 68 and 69, the jacket of the sonde has a middle portion 72 without any roughness or other irregularities which defines, with the casing 44, the annular interval 74 in which a stable upward flow of the production fluids can be established in the direction of the arrow 76, the composition of which undergoes only minimum disturbance by the presence of the sonde.

Toward the lower end of this middle part 72 of the jacket 70, the sonde 60 has an X-ray emitting device 80. Over and at a first predetermined distance $L_1$ from the emitter 80 is mounted a first receiver 82. A second receiver 84 is provided at a second predetermined distance $L_2$ from the emitter 80 greater than the first distance. A screen 79, opaque to X-rays, is placed between the generator 80 and the detector 82.

The X-ray generator 80 (FIG. 5) includes an elongated enclosure 81 which is hermetically closed and contained within the jacket 70. Inside the enclosure 81 prevails a suitable vacuum for the generation of X-rays by electron bombardment of a target. On one of the ends 83 of the enclosure 81 is mounted a cathode device 85 comprising in particular a filament 86 whose end 87 is connected to the ground of the tool. This filament is surrounded by an electrode (Wehnelt) which makes it possible to adjust the intensity of the X-ray flux.

On the other end, the wall 92 of this enclosure 81 is traversed coaxially by a massive anode 94 whose widened end 96 terminates in a plate 95 perpendicular to its axis. This plate forms the X-ray generating target for the electron beam produced by the cathode 86 and focused by the electrode 88 when the end 98 of the anode 94 outside the enclosure 81 is supplied by a high positive dc voltage produced by a generator 100 (FIG. 4) of about 10 watts housed inside the jacket 70 under the emitter 80. This generator is supplied from the surface with alternating current via two conductors inside the cable 62 and can produce a high dc voltage capable of being modulated and of rising to a value of about 100 kilovolts with a current of about 100 micro-amperes, or even 150 kilovolts, depending on requirements.

The tubular enclosure 81 includes, in its intermediate part, a cylindrical beryllium window 104 connected hermetically by cylindrical seals 105 and 106 to the respective upper and lower ends of the enclosure 81 (which are made, in this example, of glass or ceramic).

In the operational position shown in the drawings, the lower seal 106 of the beryllium window 104 is located in a plane below the plane of the plate 95. It thus allows the passage of the X-rays produced in directions practically tangential to the plane of this plate, such as the direction 110. Its height is sufficient to allow the exit of the radiation produced by the target 95 within a solid angle of about 75° to form a beam of revolution around the axis of the tube delimited schematically in the drawing of FIG. 5 by lines 110 and 112.

Opposite the window 104, the jacket 70 comprises a thick cylindrical beryllium window 116 whose axial dimension is sufficient to allow the passage of the beam delimited by the cones of lines 110 and 112. The thickness of this window is determined to enable it to withstand pressures of 1400 bars and temperatures of 175° C. It is covered on the outside with a layer of epoxy for protection.

The X-ray generator 80 makes it possible to produce a photon output flux with energies equal to or higher than 20 kev and more than $10^{11}$ photons per second in a volume compatible with utilization conditions in a logging tool. In one embodiment, the diameter of the enclosure 81 is slightly smaller than 3 cm and the anode-cathode distance over which the electrons are accelerated is smaller than 10 cm.

The curves 120 and 121 of FIG. 6 represent the energy spectra of the photons received by one of the detectors after interaction respectively with a pure petroleum and with salt water for a constant power supply voltage of the generator equal to 100 kev. These curves define the respective reception rate of the photons represented in number of counts per second on the ordinate as a function of their energy in kilo-electron-volts on the abscissa. These continuous spectra extend between a lower value slightly below 20 kev, the transmission limit of the beryllium windows 104 and 116, up to a maximum energy value of 100 kev.

Each of the receivers 82 and 84 includes (FIG. 4) a scintillation detector respectively 130 and 132 made up of a sodium iodide crystal housed within a respective compartment delimited along the jacket 70 by a respective beryllium window 131 and 133 (FIG. 4), the specifications of which are similar to those of the window 116 of the generator 80.

The receivers 82 and 84 each include a photomultiplier, respectively 134 and 136, connected to the outputs of the detectors 130 and 132. The outputs 135 and 137 of the photomultipliers 134 and 136 are connected by conductors (not shown) to a signal processing cartridge 140 placed at the upper part of the sonde over the second receiver 84.

In FIG. 7 has been represented schematically a processing circuit at the output of the receivers 82 and 84. Each pulse at the output 145 of the photomultiplier 134 has an amplitude proportional to the energy of the photon detected by the detector 130. Each pulse is shaped by a preamplifier 146.

After shaping by the preamplifier 146, the pulses are applied to the input 151 of a voltage discriminator 150. This discriminator has two outputs 152 and 154. On the output 152 appears a signal $I_1$ (L) proportional to the number of photons captured per second by the detector 130 within a "low" energy interval around 30 kilo-electron-volts represented by L in FIG. 6. The output 154 of the discriminator 150 produces a signal $I_1$ (H) with an amplitude proportional to the count rate of the photons captured by the receiver 82 within a "high" narrow energy band centered on 60 kilo-electron-volts, represented by the letter H in FIG. 6. For this purpose, the discriminator 150 includes a battery of voltage comparators whose levels $V_1(H)$, $V_2(H)$ on the one hand, and $V_1(L)$ and $V_2(L)$ on the other (see FIG. 6), define two voltage ranges corresponding respectively to the "high" and "low" energy intervals of the photons received. There is a counter at the output of each pair of comparators for the pulses received within the respective voltage ranges. The counters condition the signals $I_1$ (H) and $I_1$ (L) for transmission by the cable 62 to the surface instrumentation.

Similarly, the output 155 of the photomultiplier 136 is connected to a preamplifier 156 at the input 161 of a discriminator 160 which delivers on its outputs 162 and 164, respectively, two signals $I_2$ (L) and $I_2$ (H) corresponding respectively to the count of the photons received within the energy intervals $L_o$ and $H_o$.

The output signals of the discriminators 150 and 160 are transmitted to an encoder 172 before being sent via the telemetering system along the cable 62 to a decoder 174 belonging to the surface instrumentation. This instrumentation is adapted to produce a measurement of the attenuation of the photons in the intervals $L_o$ and $H_o$ over the distance D separating the receivers 82 and 84.

Very schematically, FIG. 7 represents the functions of this instrumentation by four logarithmic amplifiers 175 to 178 which produce output signals representative of the parameters Log $I_1$ (L), Log $I_1$ (H), Log $I_2$ (L) and Log $I_2$ (H), respectively. These signals are subtracted two by two in circuits 180 and 182 which deliver on their respective outputs 181 and 183 signals L' and H', transmitted to the input of a processing unit 184.

In operation, a continuous spectrum radiation emitted by the X-ray generator 80 interacts with the fluid filling the annular space between the sonde 60 and the casing over a distance $L_1$ between the generator 80 and the first detector 130, on the one hand, and over a distance $L_2$ between this generator 80 and the second detector 132, on the other.

The intensity of the radiation captured by each of the receivers 82 and 84 within a given energy interval depends on the portion of the incident photons absorbed by the medium studied in this interval. For each of the first and second receivers 82 and 84, the respective intensity $I_1$ and $I_2$ in this energy interval can be expressed by the following relationship:

$$I_1 = I_o \Omega_1 \rho e^{-\mu t L_1} \quad (9)$$

$$I_2 = I_o \Omega_2 \rho e^{-\mu t L_1}$$

$$D = L_2 - L_1$$

In this relationship, $I_o$ is the intensity which would correspond to a zero interaction attenuation, $\Omega_1$ and $\Omega_2$ are constants characteristic of the first and of the second receivers, and D is the distance between the two receivers.

In the example considered, the distances $L_1$ and $L_2$ are respectively 0.12 m and 0.32 m.

After the dicrimination of the photons received in the two distinct high and low energy interals, H and L, the calculation carried out by the surface instrumentation furnishes:

$$H' = \text{Log} \frac{I_1(H)}{I_2(H)} = k + \mu_t(H) \times D \quad (10)$$

$$L' = \text{Log} \frac{I_1(L)}{I_2(L)} = k + \mu_t(L) \times D$$

in which k is a constant.

The presence of two detectors each furnishing an intensity $I_1$ and $I_2$ within each energy interval makes it possible to obtain ratios H' and L' which are independent of the fluctuations in the flux of incident photons on the investigated medium, due to any instabilities of the X-ray generator. It has been shown, in fact, that the fluxes received by each of the two detectors in each energy interval are directly proportional to the incident fluxes. The signals H' and L' are thus representative of the attenuation of the photon flux within the corresponding energy interval over the distance D in the medium analyzed.

Referring to equation (5), it is noted that the signal H' and L' are directly related to the parameter characteristic of the photoelectric absorption U and to the mass density $\rho$. By establishing a correspondence between parameters $H_1$ and $L_1$ and H' and L' according to the following relationship:

$$H_1 = \frac{A}{Z} (k' - H') \quad (11)$$

$$L_1 = \frac{A}{Z} (k'' - L')$$

where k' and k" are constants, the relationship between the signals obtained on the output of the circuit of FIG. 7 and the coefficients U and $\rho$ can be expressed in the following form:

$$H_1 = (\alpha U + \beta \rho) D \quad (12)$$

$$L_1 = (\alpha' U + \beta' \rho) D$$

The coefficients $\alpha$, $\beta$, $\alpha'$ and $\beta'$ depend on the considered energy interval and on the mean energy of the spectrum emitted by the X-ray generator 80. They can be determined by calibration.

Based upon the observation furnished by Table I that the parameter Z/A varies little as a first approximation according to whether the fluid is pure water, salt water or petroleum, the processing unit 180 determines (using the value of this ratio in pure water) a first value of the parameters $H_1$ and $L_1$ from which values of U and $\rho$ can be calculated or derived, as shown by the relationships (11).

At the beginning of the measurement, input data concerning he parameters $U_h$ and $\rho_h$ are furnished to the processing unit 180. These parameters can be obtained by knowing in advance the composition of the petroleum produced in the region and, more particularly, in the well and the petroleum bearing zone under consideration. They can also be obtained as indicated earlier, by a preliminary measurement in the well after stopping the flow of fluids and stabilization.

The processing unit is thus capable of deriving from the values U and $\rho$ previously obtained a first measurement of the ratio V (total water/fluid) and of the weight S of salt per unit volume of water. A finer measurement of Z/A can then be obtained from these values by the relationship:

$$\left(\frac{Z}{A}\right)_{mel} = \quad (13)$$

$$\frac{SV}{\rho}\left(\frac{Z}{A}\right)_{NaCl} + \frac{V}{\rho}\left(\frac{Z}{A}\right)_{H_2O} + \left(\frac{1-V}{\rho}\right)_{ph}\left(\frac{Z}{A}\right)_h$$

where (Z/A) NaCl, and (Z/A) $H_2O$ and $(Z/A)_h$ are respectively the values of the ratio Z/A of pure salt, of pure water, and of pure petroleum, as they are given for example in Table I. From this new value of the ratio Z/A, the processing unit carries out a precise determination of S and V by successive iterations.

The values U and $\rho$ depend on the temperature and on the pressure of the fluid, according to known laws on the basis of which the processing unit is programmed to carry out the necessary corrections.

In the embodiment just described, the power supply voltage of the X-ray generator 80 remains the same throughout the measurement. Under these conditions, the energy spectrum of the photons emitted by the X-ray tube extends continuously between approximately 20 kev and 100 kev, and the spectral selection of the high and low energy photons takes place at the level of the receivers 82 and 84 by the amplitude selector delimiting the bands $L_o$ and $H_o$ in the discriminators 150 and 160.

According to another embodiment, the measurement is carried out by modulating the energy of the photons emitted. It is possible, for this purpose, to operate the generator in the pulsed mode by supplying it with pulses of different voltage levels. Thus, in a first phase, the generator emits a first relatively high energy pulse with a duration of about 20 ms and a power supply voltage of about 100 kV. The spectrum of the emitted radiation then corresponds to the curve 190 of FIG. 10. The mean energy $\hat{E}_1$ of this spectrum is about 60 kev corresponding to the point 192 of the curve 190.

Figure 10:
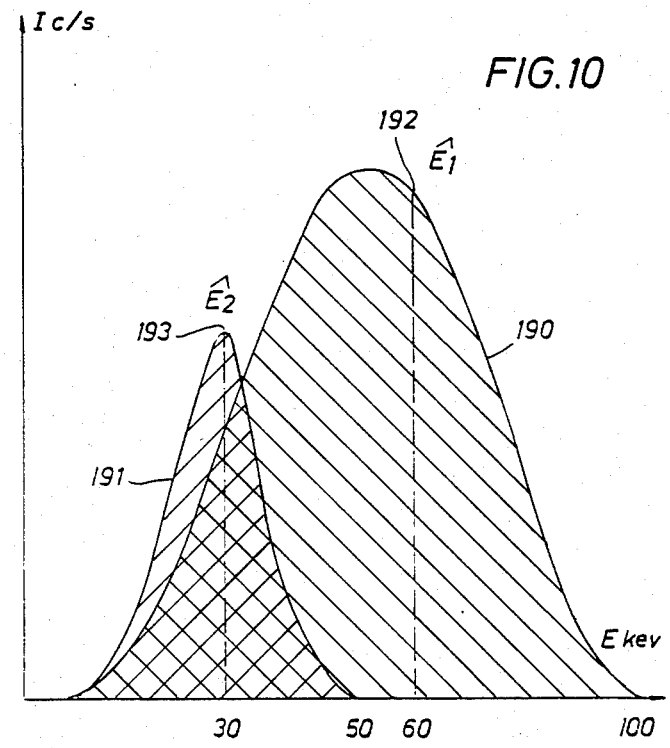
FIG. 10 illustrates two energy spectra of different photons emitted successively by the same source.

In a second phase, the X-ray generator 80 is supplied with a voltage of 50 kV to produce a second relatively low energy pulse whose spectrum is represented by the curve 191 of FIG. 10. The maximum intensity of this spectrum corresponds substantially to a mean photon energy of about $\hat{E}_2 = 30$ kev, as represented by the point 193 of curve 191.

Instead of counting the pulses produced during each window at the output of the photomultipliers 134 and 136, the total intensity of the radiation captured by the detectors 130 and 132 is measured (FIG. 8). In fact, as the count rates of the detectors 130 and 132 are very high, it is no longer possible to obtain a spectral analysis of the photons. The respective values of the currents $I'_1$ and $I'_2$ respectively available at the outputs 145 and 155 of the photomultipliers are nevertheless representative of the photon fluxes corresponding to the energies $\hat{E}_1$ and $\hat{E}_2$. The signals $I'_1$ and $I'_2$ are converted directly by respective logarithmic amplifiers 202 and 204 whose outputs are connected to the respective inputs 203 and 205 of a differential amplifier 206 which delivers at its output 208 a signal proportional to Log $I'_1/I'_2$ throughout the duration of each high and low energy pulse. The signals H' and L' appearing successively at the output 208 in correspondence with the high and low energy pulses are transmitted to the surface for processing.

In order to compensate for any drift in the gain of the photomultipliers and of the logarithmic ampifiers, provision is made for the use of a light-emitting diode (not shown) which is connected to the input of each of the two photomultipliers 134 and 136 by optical fibers within the jacket 70. The power supply voltage of the photomultiplier 136 is adjusted by a circuit 210 (FIG. 8) connected between the output 208 of the differential amplifier 206 and an input 212 controlling the high voltage of the photomultiplier 136 so as to keep constant, throughout the dark periods of the generator 80, the function Log $I'1$ ref/$I'2$ ref of the currents $I'_{1ref}$ and $I'_{2ref}$ obtained, respectively, at the outputs 145 and 155 of the photomultipliers in response to a luminous reference pulse produced by the light-emitting diode.

In FIG. 9 have been represented schematically the levels of the pulse signals 220, 222 and 224 at the output 208 as a function of time in response respectively to a first energy pulse emitted at a "low" voltage and then a second energy pulse emitted at a "high" voltage, and then a reference diode excitation pulse. Each of these pulses has a duration of about 20 ms. They are separated by dark intervals of about 20 ms, for a total sequence time of about 100 ms.

The power supply of the X-ray generator in the pulsed mode has the advantage of limiting the power dissipation of the tube. It also makes it possible to reduce the influence of the dark currents of the photomultipliers 134 and 136 at high temperature, i.e. currents in the absence of radiation on the detectors 130 and 132. The signal/noise ratio of the measurement is thus substantially improved.

In addition, the generator pulse excitation method lends itself well to the use of semiconductor detectors, for example using cadmium telluride or mercuric iodide, of small size, owing to the high level of the intensities $I'_1$ and $I'_2$ collected. These detectors can in particular be advantageous for the measurement of the homogeneity of the fluid analyzed, in particular in deviated wells.

The use of an X-ray generator such as the emitter 80 within the framework of a measurement in a petroleum well in production is of value because, unlike chemical sources (such as a radioactive isotope), it does not present the risk of contaminating the well in case the sonde should be lost (a rare occurrence but one which cannot be totally excluded).

An X-ray generator such as the generator 80 also offers the advantage of furnishing a high photon flux, consequently allowing rapid measurements for the dynamic study of flows. The accuracy of the measurements obtained depends on the count rate of the detector used. The use of a high photon flux source is thus a favorable factor in this respect.

It is also possible to use the X-ray generator 80 while modulating the acceleration voltage of the electrons on the anode 94 (FIG. 5) of the tube 80 in a manner which can be continuous and nonpulsed. For an acceleration voltage $V_0$, the mean energy of the photons emitted is $\hat{E} = \frac{2}{3} e V_0$ (where e is the electron charge). If the acceleration voltage is made to vary around the voltage $V_0$, there is the possibility of acting on this mean energy E and of thereby varying the extent of the photoelectric absorption of the medium considered. The signal measured on a detector 82 or 84 then has the following form:

$$I_D = I_0 \Omega \, \sigma \, e^{-(\alpha U + \beta \rho)D}$$

with $$\alpha = \alpha_o (\hat{E}/\hat{E}_o)^{-3}$$

$\beta$ varying little with the energy of the X photons.

By modulating with a sinusoidal voltage signal the energy of the photons, using a modulation rate of $-\Delta \hat{E}/\hat{E}_0$ (where $\hat{E}_0$ corresponds to the voltage $V_0$), one obtains:

$$I_D = I_0 \Omega \rho e^{-\{\alpha_o(1 + \frac{\Delta \hat{E}}{E_o} \sin \omega t)3 U + \beta \rho\} D}$$

The signal at the output of the detector is thus a current made up of a mean component which depends on several variables, including the density of the medium, and of a sinusoidal component which depends essentially on the photoelectric absorption coefficient U of this medium.

In FIG. 11 has been represented the curve 195 of variations as a function of time in the current $I_D$, obtained at the output 208 of the amplifier 206 of FIG. 8. This signal is affected by rapid variations at the modulation frequency of the power supply voltage of the X-ray generator superposed on a mean value $I_{DO}$ represented by a broken-line curve in FIG. 11 and whose value varies in particular as a function of the density. The amplitude $\Delta I_D$ of the sinusoidal modulation superposed on the mean amplitude $I_{DO}$ is, on the contrary, essentially a function of the photoelectric absorption coefficient U. Thus, the filtering of the signal by means of lowpass and highpass filters (not shown) makes it possible to separate the dc component $I_{DO}$ and the ac component of amplitude $\Delta I_D$ to obtain a direct measurement of the values $\rho$ and U.

Thanks to the use of photoelectric absorption, the accuracy of the measurement of the water/petroleum ratio is substantially improved in relation to that which can be obtained by the density measurement alone. The measurement of the value L' carried out at "low" energy is in fact about four times more sensitive to variations in this ratio than the measurement obtained at "high" energy. Thus, for example, for a variation of 1% in the total water/fluid ratio V, corresponding to a density variation of 0.002 g/cm$^3$, the respective variations dH'/H' and dL'/L' in the values H' and L' are 0.7% and 2.6%.

The measurement also makes it possible to determine precisely the salinity of the formation water. The measurement of L' at "low" energy is in fact about ten times more sensitive to variations in salinity than the measurement at "high" energy. It makes it possible in particular to detect variations corresponding to 1.5 kg of salt per m$^3$ of crude petroleum (10$^3$ liters) whereas the corresponding density variation is in general not detectable.

Such a precise measurement of salinity is advantageous particularly for detecting excessive salt production in the flow of petroleum obtained from a given producing stratum. It also allows precise monitoring of water injection techniques in petroleum bearing strata for better production efficiency.

Finally, a tool such as the one described, with an X-ray generator and detectors (FIG. 3) can be applied to the study of flow conditions in a petroleum well in production, thanks to the speed of the measurements possible. This speed in fact makes it possible to detect the displacement of heterogeneity zones such as oil bubbles in water, or gas in the liquid between the first and the second detector.

I claim:

1. A method for measuring the absorption of a photon flux by the fluid flowing in an oil well lined with a metal casing to produce measurements related to the composition of the fluid, comprising the steps of lowering in the well an elongated sonde having a photon source and at least one detector disposed at longitudinally spaced locations, producing by means of the source a photon flux with an energy spectrum below such a predetermined level that the walls of the metal casing substantially absorb the photons impinging thereon, said flux including first photons with a low energy level at which photoelectric absorption is significant and second photons with a high energy level at which Thomson scattering is predominant, directing the photon flux to irradiate the fluid surrounding the sonde symmetrically about its axis, detecting by means of said at least one detector the resultant photon flux produced by the interaction of the emitted flux with the fluid and deriving from the output of said at least one detector first and second measurements representatives of the absorptions of said first and second photons, respectively, said measurements being indicative of the photoelectric absorption coefficient and the density of the fluid.

2. The method of claim 1, wherein the energy of the emitted photons is lower than 100 kev.

3. The method of claim 1 or 2, wherein a photon flux with a continuous energy spectrum is produced by means of an X-ray generator.

4. The method of claim 3, further comprising the step of detecting the resultant photon flux by means of another detector longitudinally spaced from the one detector by a predetermined distance, and combining the outputs of the one and the other detector in such manner that said first and second measurements are representative of the absorption over the predetermined distance in the fluid, the measurements thus obtained being independent of fluctuations in the flux produced by the x-ray generator.

5. The method of claim 3, wherein the X-ray generator is operated to continuously produce a predetermined energy spectrum including said low energy level and said high energy level, and the resultant flux is measured within first and second predetermined energy windows to discriminate between said first and second photons and produce said first and second measurements indicative of the photoelectric absorption coefficient and of the density of the fluid.

6. The method of claim 5, wherein the first and second energy windows are respectively centered about 30 kev and 60 kev.

7. The method of claim 3, wherein the X-ray generator is operated to produce a photon flux with an energy spectrum varied with time in accordance with a predetermined time function between a first predetermined energy spectrum having a mean energy for which photoelectric absorption by the fluid is significant and a second predetermined energy spectrum having a mean energy for which Thomson scattering is predominant.

8. The method of claim 7, wherein the detection step comprises the detection of the total intensity of the resultant photon flux.

9. The method of claim 8, wherein the predetermined time function is a sinusoidal function, whereby the produced measurement has a mean value indicative of the density of the fluid and periodic variations about the mean value the amplitude of which is indicative of the photoelectric absorption coefficient of the fluid.

10. The method of claim 7, wherein the X-ray generator is operated to alternately produce a first photon flux with the first predetermined energy spectrum and a second photon flux with the second predetermined energy spectrum, and the resultant first and second photon fluxes are alternately detected in timed relationship with the alternate operation of the X-ray generator.

11. The method of claim 7, wherein the first and second predetermined energy spectra have respective mean values of 30 kev and 60 kev.

12. A method for analyzing the fluid flowing in an oil well lined with a metal casing, the fluid comprising a mixture of oil and saline water, comprising the steps of lowering in the well an elongated sonde having a photon source and at least one detector disposed at longitudinally spaced locations, producing by means of the source a photon flux with an energy spectrum below such a predetermined level that the walls of the metal casing substantially absorb the photons impinging thereon, the emitted flux including first photons with a first energy range at which photoelectric absorption is significant and second photons with a second energy range at which Thomson scattering is predominant, directing the photon flux to irradiate the fluid surrounding the sonde symmetrically about its axis, detecting by means of said at least one detector the photons emitted at the first energy range and the photons emitted at the second energy range in the resultant photon flux produced by the interaction of the emitted flux with the fluid, deriving from the output of said at least one detector first and second measurements, combining the measurements to derive the photoelectric absorption coefficient and the density of the fluid mixture, and deriving from the coefficient and the density the respective amounts of water and oil and the salinity of the water.

13. A well logging sonde for displacement in an oil well lined with a metal casing for producing measurements related to the composition of the well fluid, comprising:

an elongated body for displacement in the well, a photon source at a first location on said body for producing a photon flux with an energy spectrum below such a predetermined level that the walls of the metal casing substantially absorb the photons impinging thereon, said photon flux comprising first photons with a low energy level at which photoelectric absorption by the fluid is significant and second photons with a high energy level at which Thomson scattering is predominant, at least one photon detector at a second location on said body longitudinally spaced from said first location, a photon-absorbing shield on said body interposed between the source and the detector, means for directing the flux from the source outwardly of the body towards said detector symmetrically about the body, and means for deriving said measurements from the output of said detector, said deriving means comprising spectral selection means providing first and second measurements in response to the detection of said first and second photons, said measurements being indicative of the photoelectric absorption coefficient and of the density of the fluid.

14. The sonde of claim 13, wherein said photon source is operable to produce a photon flux with an energy spectrum below 100 kev.

15. The sonde of claim 13 or 14, wherein said photon source comprises a X-ray generator including a photon generating unit operable to produce a photon flux with a continuous energy spectrum upon high voltage energization and a supply unit operable to energize said photon generating unit.

16. The sonde of claim 15, further comprising another detector on said body longitudinally spaced from said one detector by a predetermined distance.

17. The sonde of claim 15, wherein said supply unit is operable to continuously produce such a voltage that the photon flux includes said first photons and said second photons, and said spectral selection means is responsive to the detection of photons within respectively first and second predetermined energy windows related to said low and high energy levels, respectively.

18. The sonde of claim 15, wherein said supply unit is operable to produce a voltage varied with time in accordance with a predetermined time function between a low value and a high value, said values being such that, at the mean value of the energy spectrum, photoelectric absorption is significant where said low value is applied and Thomson scattering is predominant where said high value is applied.

19. The sonde of claim 18, wherein said deriving means is operable to provide a measurement of the total intensity of the resultant photon flux.

20. The sonde of claim 18, wherein said supply unit is operable to alternately produce said low and said high voltages in the form of voltage pulses.

21. The sonde of claim 18, wherein said time function is a sinusoidal function.

22. The sonde of claim 18, wherein said low voltage is about 50 kv and said high voltage is about 100 kv.

* * * * *